(12) United States Patent
Huang

(10) Patent No.: US 6,893,465 B2
(45) Date of Patent: May 17, 2005

(54) VIVIDLY SIMULATED PROSTHETIC INTERVERTEBRAL DISC

(75) Inventor: Shih-Shing Huang, Taipei (TW)

(73) Assignee: Shi, Tain-Yew, Taipei (TW)

( * ) Notice: Subject to any disclaimer, the term of this patent is extended or adjusted under 35 U.S.C. 154(b) by 100 days.

(21) Appl. No.: 10/407,075

(22) Filed: Mar. 31, 2003

(65) Prior Publication Data

US 2004/0193273 A1 Sep. 30, 2004

(51) Int. Cl.[7] .................................................. A61F 2/44
(52) U.S. Cl. .................................................. 623/17.12
(58) Field of Search ........................... 623/11.11, 16.11, 623/17.11–17.16, 20.16, 20.17, 23.34, 23.56, 23.57, 23.75, 23.76, 23.51, 23.6, 23.61, 23.63; 606/60, 61, 76, 77, 69, 70, 71

(56) References Cited

U.S. PATENT DOCUMENTS

| | | | | |
|---|---|---|---|---|
| 4,309,777 A | * | 1/1982 | Patil | 623/17.13 |
| 4,961,740 A | * | 10/1990 | Ray et al. | 606/61 |
| 5,609,635 A | * | 3/1997 | Michelson | 623/17.16 |
| 5,707,962 A | * | 1/1998 | Chen et al. | 514/12 |
| 5,928,284 A | * | 7/1999 | Mehdizadeh | 623/17.13 |
| 6,039,762 A | * | 3/2000 | McKay | 623/17.11 |
| 6,165,486 A | * | 12/2000 | Marra et al. | 424/423 |
| 6,371,988 B1 | * | 4/2002 | Pafford et al. | 623/17.11 |
| 6,454,806 B1 | * | 9/2002 | Cohen et al. | 623/17.15 |
| 6,514,286 B1 | * | 2/2003 | Leatherbury et al. | 623/11.11 |
| 6,599,323 B2 | * | 7/2003 | Melican et al. | 623/23.72 |
| 6,770,695 B2 | * | 8/2004 | Ricci et al. | 524/423 |
| 2002/0035400 A1 | * | 3/2002 | Bryan et al. | 623/17.15 |

* cited by examiner

Primary Examiner—Eduardo C. Robert
Assistant Examiner—Anuradha Ramana

(57) ABSTRACT

A prosthetic intervertebral disc includes an upper fusion member adapted to be gradually fused and secured to an upper vertebra, a lower fusion member adapted to be gradually fused and secured to a lower vertebra, and a restorable cushioning coupler retained in between the upper and lower fusion members, whereby upon bending or twisting of a patient's spine, the upper and the lower fusion members may be flexibly moved with each other for enhancing free movement of the patient's spine and body, safely resiliently cushioned and easily restored by the cushioning coupler in between the upper and lower fusion members.

8 Claims, 4 Drawing Sheets

VIVIDLY SIMULATED PROSTHETIC INTERVERTEBRAL DISC

BACKGROUND OF THE INVENTION

It is known that an artificial intervertebral disc may be provided for replacing diseased or damaged disc for the treatment of spinal or back pain diseases. Conventional disc prostheses generally consist of two metal endplates and a flexible core in between mimicking the nucleus of the disc.

U.S. Pat. No. 4,309,777 disclosed a disc having a plurality of springs positioned between an upper disc and a lower disc. Each upper or lower disc is formed as a short cylinder. Whenever bending the body, the two discs may be dogged with each other to lock their flexible movement to thereby influence the smooth movement of the spine.

U.S. Pat. No. 5,370,697 disclosed an elastic separator in between an upper and a lower support. However, the acute edges (17) on the upper and lower supports may damage the spinal nerve especially when the insert part (5) is bursted.

U.S. Pat. No. 5,562,738 disclosed a ball and socket for the disk device, which however does not provide any outer protective cover (or covers) for restraining the insert materials in the disk once burst or bulkiness is caused.

U.S. Pat. No. 5,674,296 disclosed a resilient nucleus surrounded by two concaval-convex shells in the disc prosthesis. The nucleus may be freely slipped within the two shells to influence its supporting stability of the disc.

U.S. Pat. No. 5,824,093 disclosed one or two hydrogel capsules in the prosthetic disc. Since the capsules (10) are formed as elongated shaped and easily slipped, they can not support the body weight homogeneously and stably.

U.S. Pat. No. 6,368,350 disclosed two bearing surfaces formed in the disc prosthesis for a rotational freedom. However, once the two bearing surfaces are abnormally biased or dislocated, how can they be normally restored automatically? Meanwhile, it is lacking of any cushioning mechanism for mimicking the disc nucleus.

U.S. Pat. No. 6,395,032 disclosed a flexible seal extending between two opposing plates of the disc prosthesis having liquid provided in a closed chamber between the two plates. There is no safety means provided for preventing from the burst of the disc. A catastrophe may occur to seriously injure the patient once the disc is bursted.

The present inventor has found the drawbacks of the conventional prosthesis discs and invented the present prosthetic intervertebral disc for vividly simulating a true disc.

SUMMARY OF THE INVENTION

The object of the present invention is to provide a prosthetic intervertebral disc including an upper fusion member gradually fused and secured to an upper vertebra, a lower fusion member gradually fused and secured to a lower vertebra, and a restorable cushioning coupler retained in between the upper and lower fusion members, whereby upon bending or twisting of a patient's spine, the upper and the lower fusion members may be flexibly moved with each other for enhancing a free movement of the patient's spine and body, as resiliently cushioned and easily restored by the cushioning coupler in between the upper and lower fusion members.

Another object of the present invention is to provide a prosthetic intervertebral disc having protective device to support the upper and lower vertebrae at a minimal height to prevent from collapse or bulkiness of the core as inserted in between the upper and lower vertebrae to prevent from catastrophe injury to the patient.

DETAILED DESCRIPTION

Figure 1:
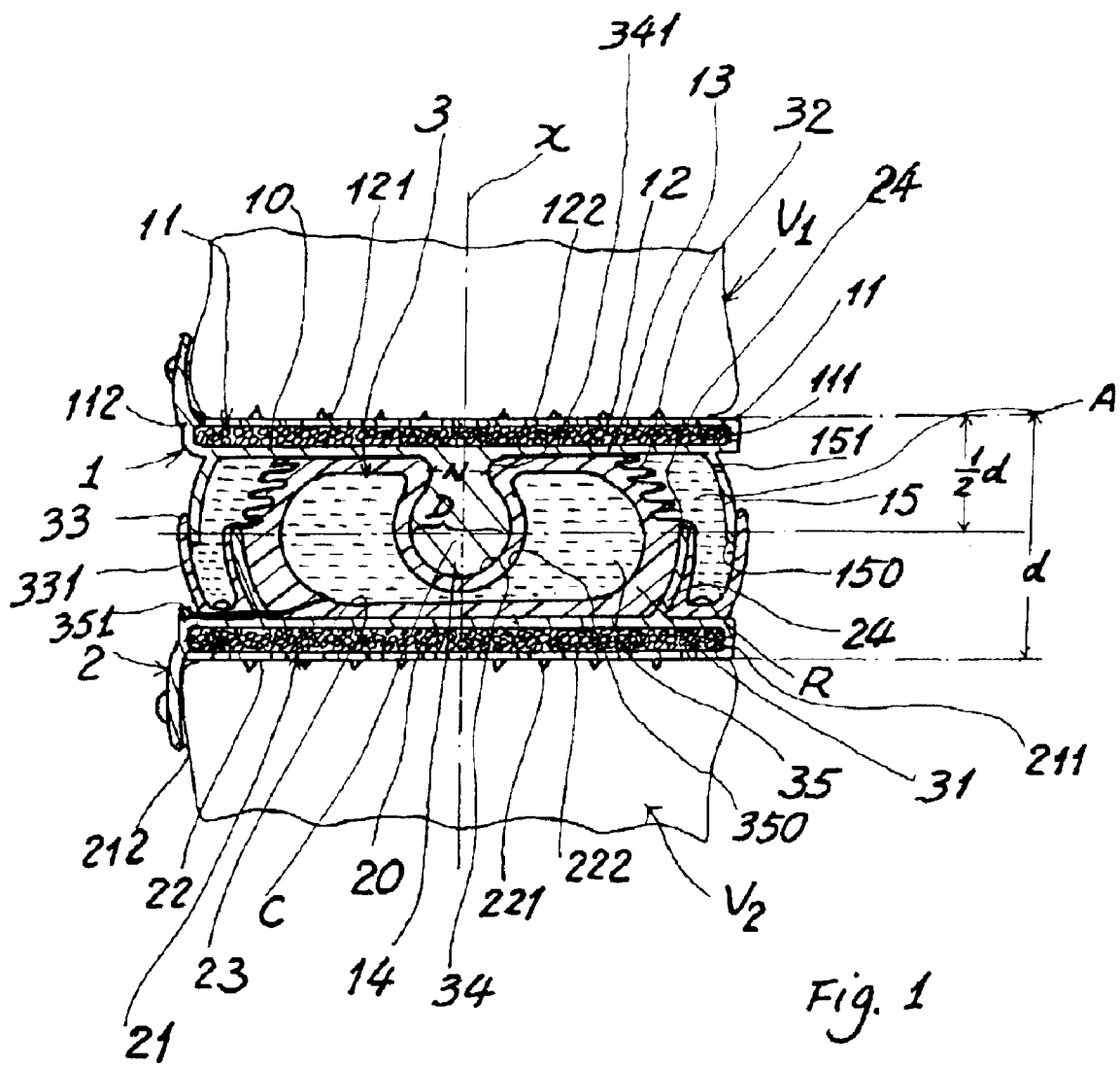
FIG. 1 is a sectional drawing of the present invention.

As shown in FIG. 1, a first preferred embodiment of the prosthetic intervertebral disc of the present invention comprises: an upper fusion member 1 secured to an upper vertebra $V_1$, a lower fusion member 2 secured to a lower vertebra $V_2$ adjacent the upper vertebra $V_1$, and a restorable cushioning coupler 3 formed in between the upper and the lower fusion members 1, 2 for resiliently coupling the upper and lower fusion members 1, 2 for resiliently connecting the upper and lower vertebra $V_1$, $V_2$ accordingly; having a longitudinal axis X defining at the longitudinal center of each upper or lower fusion member 1, 2.

The upper fusion member 1 includes: an upper fusion cage 11 having a biodegradable fusion composition 10 filled or preformed in the upper fusion cage 11, an upper implanting plate 12 formed on an upper (or top) portion of the upper fusion cage 11 to be secured to an end plate of the upper vertebra $V_1$, a base plate 13 formed on a bottom portion of the upper fusion cage 11 having a pivoting ball 14 axially protruding downwardly from the base plate 13 about a longitudinal axis X of the prosthetic disc and having an outer skirt 15 generally spherically shaped and protruding downwardly from the base plate 13 for protectively surrounding the restorable universal cushioning coupler 3 in cooperation with an inner skirt 24 protruding upwardly from the lower fusion member 2.

The upper fusion cage 11 is formed with a least a drainage hole 111 for discharging the liquid as biodegraded from the biodegradable composition 10 filled in the upper fusion cage 11, and having at least a lug 112 protruding upwardly from the cage 11 to be secured to the upper vertebra by a bolt.

The implanting plate 12 is formed with a plurality of teeth 121 protruding upwardly to be fastened to the upper vertebra $V_1$, and a plurality of fusion holes 122 formed through the implanting plate 12 to allow the bone ingrowth from the upper vertebra $V_1$ into the upper fusion cage 11.

The height of the outer skirt 15 of the upper fusion member 1 is equal to or preferably slightly larger than a half distance (½ d) of the distance (d) spaced in between the upper and lower vertebrae $V_1$, $V_2$.

The outer skirt 15 defines a curvature having its center C aligned with the longitudinal axis X of the prosthetic intervertebral disc of the present invention when normally positioned in between the upper and lower vertebrae.

The pivoting ball 14 is axially protruded downwardly from the upper fusion member 1 about the longitudinal axis X of the intervertebral disc, and having a center of the ball 14 preferably aligned with the center C of the curvature of the outer skirt 15.

The lower fusion member 2 includes: a lower fusion cage 21 having a biodegradable fusion composition 20 (same to the composition 10) filled or preformed in the lower fusion cage 21, a lower implanting plate 22 formed on a bottom portion of the lower fusion cage 21 to be secured to an end plate of the lower vertebra $V_2$, a supporting base plate 23 formed on an upper portion of the lower fusion cage 21 having an inner skirt 24 generally spherically shaped and protruding upwardly from the supporting base plate 23 to be concentric to the outer skirt 15 of the upper fusion cage 11 for engaging the restorable universal cushioning coupler 3 on the inner skirt 24 and on the supporting base plate 23 of the lower fusion member 2.

The casing of the fusion cage 11 or 21 (including all plates 12, 13, 22, 23) may be formed with bio-compatible materials including stainless steel, cobalt chrome alloy, titanium, ceramics or tantalum material, but not limited in the present invention.

The lower fusion cage 21 is formed with a least a drainage hole 211 for discharging the liquid as biodegraded from the biodegradable composition 20 filled in the lower fusion cage 21, and having at least a lug 212 protruding downwardly from the cage 21 to be secured to the lower vertebra by a bolt.

The lower implanting plate 22 is formed with a plurality of teeth 221 protruding downwardly to be fastened to the lower vertebra $V_2$, and a plurality of fusion holes 222 formed through the lower implanting plate 22 to allow the bone ingrowth from the lower vertebra $V_2$ into the lower fusion cage 21.

The height of the inner skirt 24 of the lower fusion member 2 is equal to or preferably slightly larger than a half distance (½ d) of the distance (d) spaced in between the upper and lower vertebrae $V_1$, $V_2$.

The inner skirt 24 defines a curvature having a center C aligned with the longitudinal axis X of the prosthetic intervertebral disc of the present invention when normally positioned in between the upper and lower vertebrae. The inner skirt 24 has the same curvature center C as that of the outer skirt 15.

The inner skirt 24 and the outer skirt 15 cooperatively define an annular (spherical) chamber A between the inner and outer skirts 24, 15 allowing a relative tangential movement whenever performing the bending, twisting or rotational movements of the patient's spinal vertebrae; and also providing a space for retracting (or expanding) the inner and outer skirts 24, 15 for minimally invasive surgery.

The annular chamber A as defined between the outer and inner skirts 15, 24 may be filled with buffer (viscous) liquid or lubricant which should be bio-compatible.

The outer skirt 15 may be formed with at least a communication hole 151 to provide an incoming flow of body fluid to prevent from evacuation of buffer liquid when exhausted and released outwardly through the port 331 during the "pumping" operation (which will be explained hereinafter) when bending or rotating the patient's body. The port 331 is defined between the outer skirt 15 and a sealing flap 33 integrally formed with the cushioning coupler 3 or formed on the lower fusion member 2.

The restorable cushioning coupler 3 is resiliently inserted and retained in between the upper and lower fusion members 1, 2; and majorly formed with resilient, flexible elastomer materials including polyurethane.

The restorable cushioning coupler 3 includes: a lower cushioning portion 31 secured to or integrally formed with the supporting base plate 23 of the lower fusion member 2, an upper cushioning portion 32 protruding upwardly from the lower portion 31 to be slidably contacted with the base plate 13 of the upper fusion member 1, a sealing flap 33 circumferentially formed on a lower perimeter of the cushioning coupler 3 to be slidably engageable with the outer skirt 15 of the upper fusion member 1 for shielding a free-end edge portion 150 of the outer skirt 15 and for sealing a port 331 between the sealing flap 33 and the outer skirt 15, and a spherical recess 34 recessed in a central portion of the upper cushioning portion 32 to be universally engageable with the pivoting ball 14 formed on the upper fusion member 1 for universally coupling the upper fusion member 1 with the lower fusion member 2 which is secured with or integrally formed with the cushioning coupler 3. The sealing flap 33 may be individually formed on the lower fusion member 2, and may be made of flexible weaving materials.

Figure 2:
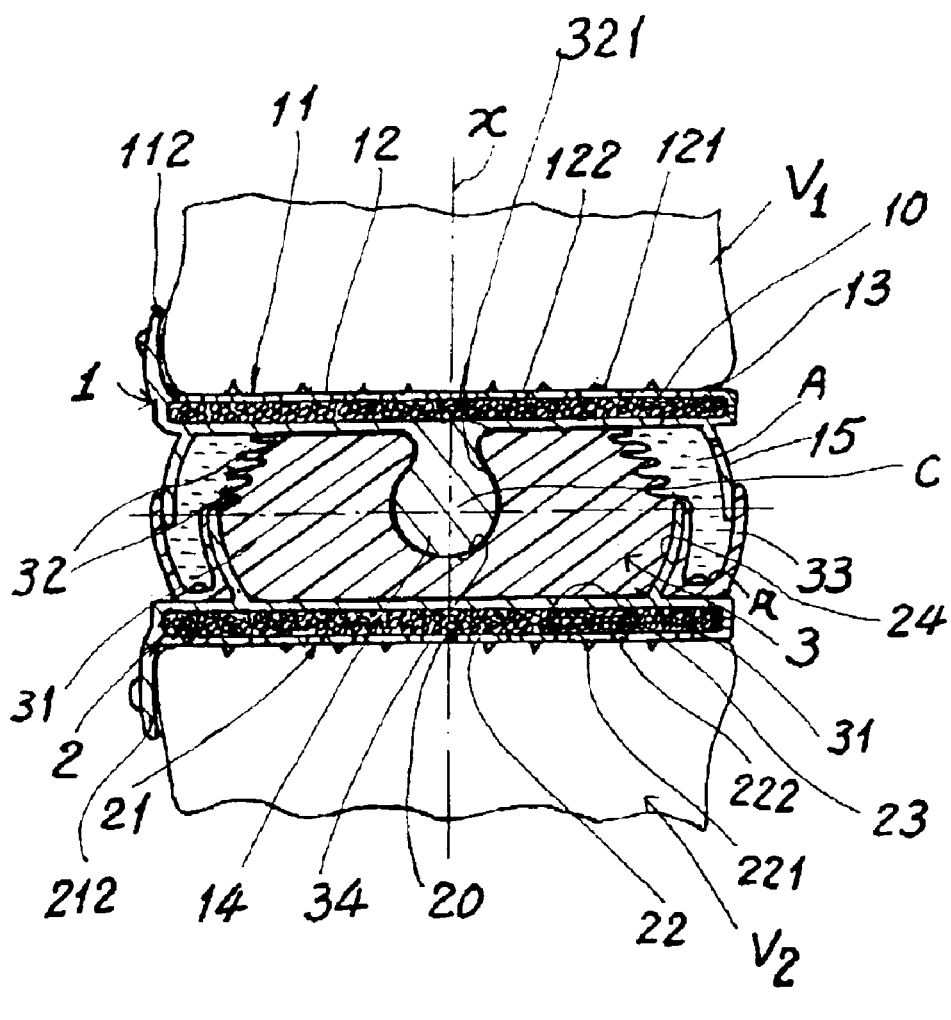
FIG. 2 is a sectional drawing showing another preferred embodiment of the present invention as modified from FIG. 1.

The lower cushioning portion 31 and the upper cushioning portion 32 may be integrally formed as a solid elastomer body without hollow portion therein as shown in FIG. 2.

The cushioning coupler 3 may be formed as a bellows to have a restoring effect to mimic a restoring spring; or having the upper cushioning portion 32 formed as a bellows as shown in FIG. 1.

The cushioning coupler 3 may be fastened to the lower fusion member 2 by adhesive bonding, riveting (as "R" as shown in FIG. 1) or molding process.

The buffer liquid as filled in the annular chamber A may also be penetrated into the interface between the upper cushioning portion 32 of the coupler 3 with the base plate 13 of the upper fusion member 1 for lubricating the rotational contacting surfaces of the two corresponding elements, including the pivoting ball 14 and the spherical recess 34.

The neck portion of the pivoting ball 14 has a diameter or width N less than the diameter D of the ball 14; and the spherical recess 34 has its narrowing port 341 having a port diameter N smaller than the diameter D of the spherical recess 34 to thereby ensure a stable coupling of the ball 14 with the recess 34.

Since the cushioning coupler 3 is made of resilient flexible material, the narrowing port 341 may be elastically expanded whenever passing the pivoting ball 14 therethrough for engaging the pivoting ball 14 with the recess 34 smoothly and conveniently.

The cushioning coupler 3 further includes a cushioning sac 35 filled with viscous liquid such as hydrogel therein, having an inflating valve 351 protruding outwardly through the lower fusion member 2 for injecting the viscous liquid into the sac 35; with the cushioning sac 35 engaged in or preformed in a hollow portion formed in the coupling coupler 3.

For minimally invasive surgery, the sac 35 is previously vacant; the coupler flattened and the two skirts 15, 24 tangentially retracted each other to minimize their volume to be as small as possible. When the present invention is inserted in between the two neighboring vertebrae, the sac 35 is injected therein with the viscous or gel-like liquid by a syringe or by a pump to expand the sac and to expand the disc in between the two vertebrae.

Naturally, the sac 35 may be integrally formed (preformed or formed in situ by foaming or molding process) in the cushioning coupler 3. Or, the sac 35 may be formed as an independent or individual element by poly-ethylene weave material surrounding its "nucleus" and the sac 35 is then engaged into the hollow portion in the coupler 3.

The sac 35 may also be formed as a tire or doughnut-shaped ring having a central recess 350 rotatably engageable with the pivoting ball 14. The sac 35 should be firmly secured or formed in the hollow portion of the cushioning coupler 3. Naturally, the shapes and structures of the sac 35 are not limited.

Figure 3:
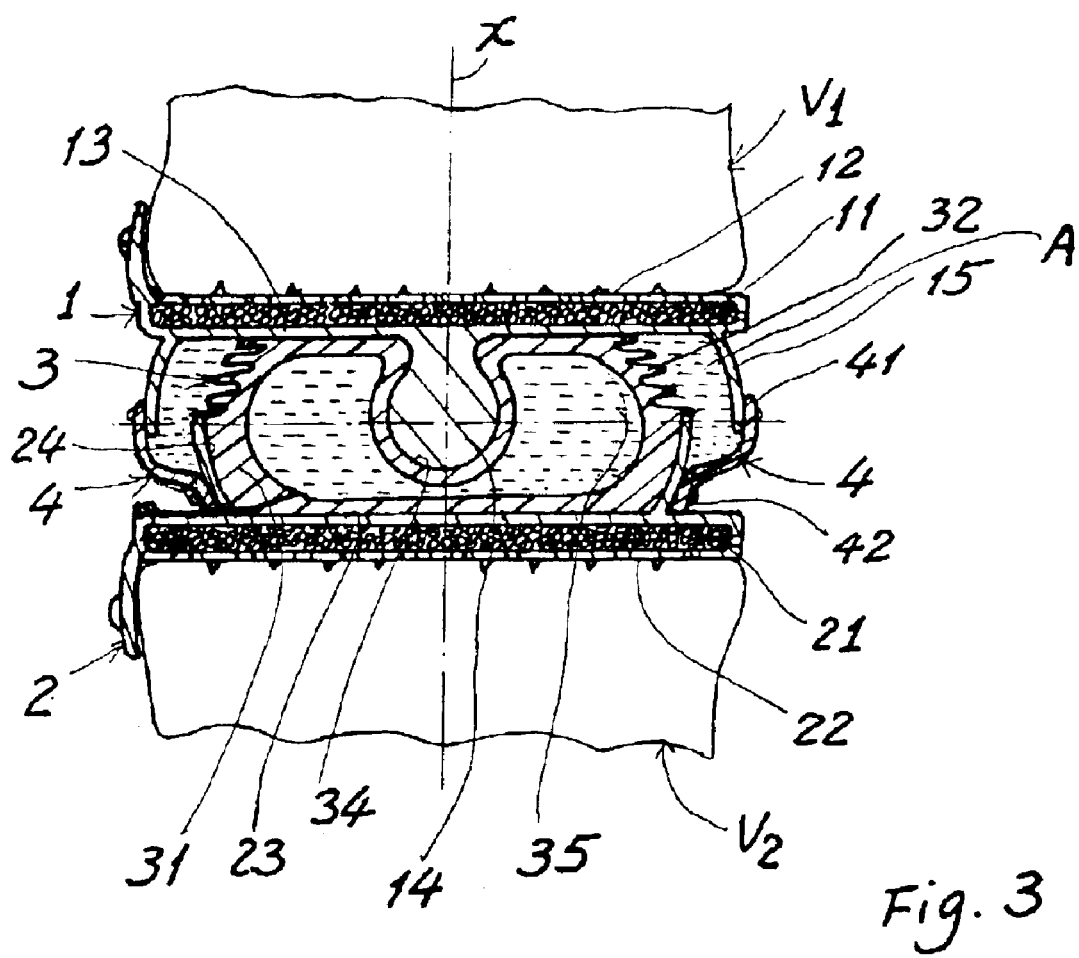
FIG. 3 is a sectional drawing of still another preferred embodiment of the present invention as modified from FIG. 1.

The outer skirt 15 and inner skirt 24 may be circumferentially connected and covered by a flexible cover 4 as shown in FIG. 3. The flexible cover 4 may be formed with poly-ethylene weave material having its upper perimeter 41 secured to the outer skirt 15 or secured to the upper fusion cage 11; and having a lower perimeter 42 of the cover 4 secured to the inner skirt 24 or secured to the lower fusion cage 21. The flexible cover 4 should be durable for bending, twisting or rotating of the vertebrae and the upper and lower fusion members 1, 2 fused thereto.

The biodegradable composition 10 or 20 comprises: hydrate of calcium sulfate, hydrate of tricalcium phosphate, hydoxyapatite, polylactic acid, elastomer or flexible ingredient and fillers. The percentage of the ingredients may be optionally adjusted depending upon the practical requirements. Naturally, the biodegradable compositions are not limited in the present invention. Other implantable fillers such as bone chips, ceramics, metal or alloy ingredients may be incorporated into such a biodegradable composition.

The present invention has the following advantages superior to the conventional intervertebral disc prostheses:
1. The disc of the present invention enables universal or flexible movements of the vertebrae to vividly mimic a true intervertebral disc.
2. Safety measures are provided to prevent from sudden collapse of a burst or bulkiness of the inserted core material between the upper and lower fusion members 1, 2, thereby preventing from catastrophe injury to a patient. Even a "collapse" occurs, the pivoting ball as shown in FIGS. 1~3, besides its universal pivoting effect, will serve as an emergency supporting column between the upper and lower vertebrae by the aid of the inner and outer skirts 24, 15, thereby preventing any subsequent serious injury or damage to the spine or spinal nerve.
3. The sac 35 filled with buffer liquid therein and the annular chamber A filled with buffer liquid therein will enhance a buffer and cushioning effect of the disc to vividly mimic the nucleus in a true disc.
4. The sealing flap 33 as tangentially shielding the outer skirt 15 will protect the edge portion 150 without contacting the spinal nerve even though the disc is accidentally deformed or collapsed. Meanwhile, the flap 33 will also temporarily "seal" the buffer liquid in the annular chamber A. During the body movements to flexibly compress or expand the bellows or the upper cushioning portion 32 of the cushioning coupler 3, the "pump" action may compress and repel the buffer liquid outwardly through the port 331 of the flap 33. Nevertheless, the body liquid will then be sucked into the annular chamber A through the hole 151 formed in the outer skirt 15, thereby balancing the liquid pressure in the chamber A without being evacuated. Such a buffer liquid in the chamber A will smoothen the operation of the moving elements and also dampening the compression and expansion of the coupler 3 for prolong its service life.
5. The sac 35 as filled with buffer liquid or the inflatable balloon 3a between the two fusion members 1, 2 may be extended after insertion in between the vertebrae to be beneficial for minimally invasive surgery.
6. The bellows 32, the sac 35 of the coupler 3 and the balloon 3a may be easily restored to prevent from unexpected dislocation of spinal vertebrae once bent or twisted. The supporting stability of the disc is better than the prior arts.
7. The biodegradable composition provides an initial strength and occupying space of the disc. Once degraded, the bone ingrowth will substitute the biodegradable composition to form a reliable fusion between the vertebrae.

The annular chamber A may also be limited as small as possibly for tangentially engaging the outer skirt 15 with the inner skirt 24. For simplifying purpose, the buffer liquid in the chamber A may also be saved and the body liquid will spontaneously enter it to render as a lubricant.

The coupler 3 may be coated, formed or reinforced with a wear-resistant surface or layer 321 (FIG. 2) on the upper surface of the upper cushioning portion 32 and the surface of the recess 34 for prolonging the service life of the coupler 3.

Figure 4:
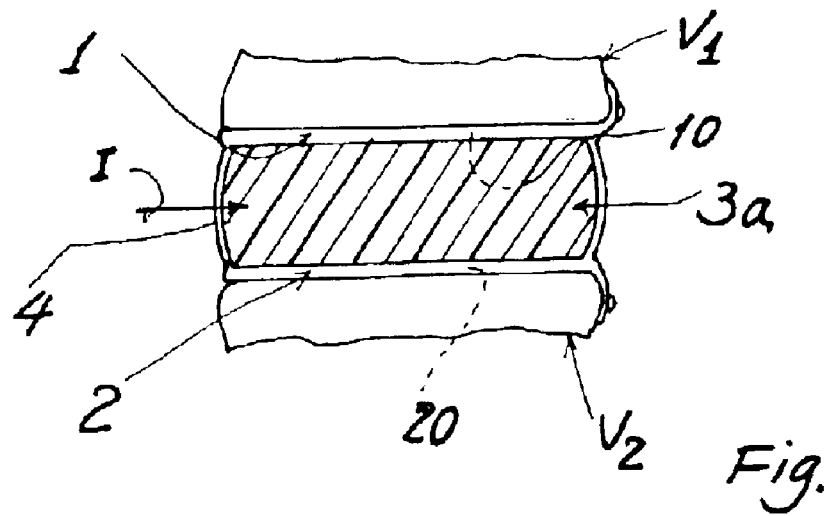
FIG. 4 shows further preferred embodiment of the present invention.

As shown in FIG. 4, the cushioning coupler 3 may be modified to be a cushioning balloon 3a as integrally formed in between the upper and lower fusion members 1, 2 having an inflatable flexible cover 4 and an elastomer foam encapsulated in the cover. For instance, a polyurethane foam may be formed in situ and instantly cured in the cover 4 in a short time. The disc can be inserted in between the upper and lower vertebrae $V_1$, $V_2$ and injected (I) with the elastomer foaming composition into the balloon 3a by instantly foaming and curing the elastomer foam to build the strength of the disc.

The polyurethane foam can be injected into the balloon 3a with two-component system, which will be instantly foaming to provide the initial supporting strength for the disc. Since the balloon can be deflated and "inflated", it is beneficial for minimally invasive surgery. The elastomer foam in the balloon 3a will render the necessary flexibility for the spinal vertebrae.

Figure 5:
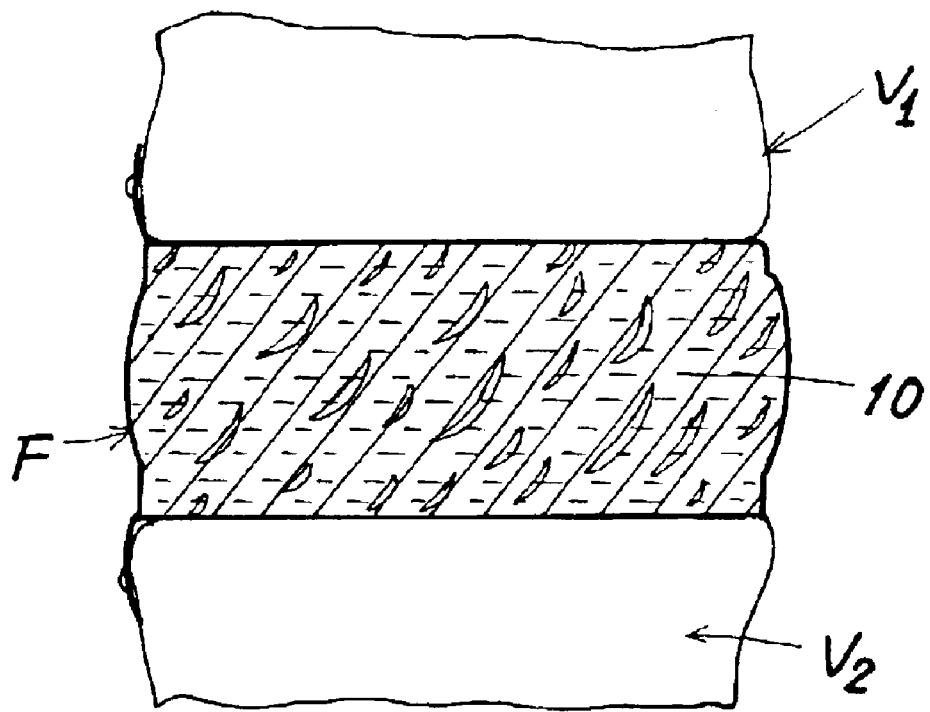
FIG. 5 shows still further preferred embodiment of the present invention.

As shown in FIG. 5, the aforementioned disc is now modified to be a fusion cage F secured between the upper and lower vertebrae $V_1$, $V_2$; having a biodegradable composition 10 formed or filled in the cage F. The biodegradable composition may be reinforced with wires (metals or polymers) to form a composite skeleton, lattice or scaffold by molding processes to be stably retained between the vertebrae. The wires may also be encapsulated with the biodegradable composition to form such a skeleton.

The biodegradable composition comprises the ingredients of different biodegrading or decomposing time periods, e.g., $CaSo_4 \cdot 2H_2O$ biodegraded with three months; $Ca_3(PO_4)_2 \cdot XH_2O$ with 6~12 months; polylactic acid with 6 months~5 years; hydroxyapatite with 2~5 years; etc. So, the initial strength of the disc is not influenced and the supporting stability for the spine is thereby not affected.

Upon the gradual periodic biodegradation or decomposition of the biodegradable composition 10 from the cage F, the bone ingrowth will fuse into the cage form either vertebra $V_1$, $V_2$ to thereby form a completely fused artificial disc for joining the upper and lower vertebrae $V_1$, $V_2$. An elastomer or flexible material may be incorporated into the composition to render a minimal flexibility for the prosthetic disc.

An average biodegradation or decomposition rate of the biodegradable composition can be varied to be generally equal to the bone ingrowth rate from either vertebra fusing into the cage F so that the biodegraded or decomposed ingredient will be substituted or occupied by the bone grown into the cage.

The present invention may be modified without departing from the spirit and scope of the present invention.

The fusion member 1 or 2 may also be simplified to be a fixing plate which is secured to either vertebra $V_1$ or $V_2$.

I claim:

1. A prosthetic intervertebral disc comprising:

an upper fusion member having a biodegradable composition filled or formed therein, and adapted to be secured to and gradually fused to an upper vertebra;

a lower fusion member having a biodegradable composition filled or formed therein and adapted to be secured to and gradually fused to a lower vertebra adjacent to the upper vertebra; and a restorable cushioning coupler resiliently formed between said upper and lower fusion members; said restorable cushioning coupler secured to one of said fusion members and flexibly engaging with the other of said fusion members to thereby flexibly couple the upper and lower vertebrae;

wherein said upper fusion member includes: an upper fusion cage having a biodegradable fusion composition filled or preformed in the upper fusion cage, an upper implanting plate formed on an upper portion of the upper fusion cage adapted to be secured to an upper vertebra, a base plate formed on a bottom portion of the upper fusion cage having a pivoting ball axially protruding downwardly from the base plate about a longitudinal axis defined at a longitudinal center of the prosthetic disc and having an outer skirt generally spherically shaped and protruding downwardly from the base plate for protectively surrounding the restorable universal cushioning coupler in cooperation with the lower fusion member; and wherein said lower fusion member includes; a lower fusion cage having a biodegradable fusion composition filled or preformed in the lower fusion cage, a lower implanting plate formed on a bottom portion of the lower fusion cage adapted to be secured to the lower vertebra, a supporting base plate formed on an upper portion of the lower fusion cage having an inner skirt generally spherically shaped and protruding upwardly from the supporting base plate to be concentric with the outer skirt of the upper fusion case for engaging the restorable universal cushioning coupler on the inner skirt and on the supporting base plate of the lower fusion member.

2. A prosthetic intervertebral disc according to claim 1, wherein said pivoting ball axially protruding downwardly from the upper fusion member about the longitudinal axis of the intervertebral disc has a center of the ball aligned with the center of curvature of the outer skirt.

3. A prosthetic intervertebral disc according to claim 1, wherein said inner skirt and said outer skirt cooperatively define an annular chamber between the inner and outer skirts allowing a relative tangential movement whenever performing a bending, twisting or rotational movement of the patient's spinal vertebrae; and providing a space for retracting or expanding the inner and outer skirts for minimally invasive surgery.

4. A prosthetic intervertebral disc according to claim 3, wherein said annular chamber as defined between the outer and inner skirts is filled with a buffer liquid which is bio-compatible.

5. A prosthetic intervertebral disc according to claim 1, wherein said restorable cushioning coupler includes: a lower cushioning portion secured to a supporting base plate of the lower fusion member, an upper cushioning portion protruding upwardly from the lower cushioning portion in slideable contact with a base plate of the upper fusion member, a sealing flap circumferentially formed on a lower perimeter of the cushioning coupler to be slidably engageable with an outer skirt of the upper fusion member for shielding a free-end edge portion of the outer skirt and for sealing a port between the sealing flap and the outer skirt, and a spherical recess formed in a central portion of the upper cushioning portion to be universally engageable with a pivoting ball formed on the upper fusion member for universally coupling the upper fusion member with the lower fusion member, said lower fusion member being formed with the cushioning coupler; said coupler having a wear-resistance layer formed on an upper surface of the upper cushioning portion and on a surface of the recess.

6. A prosthetic intervertebral disc according to claim 5, wherein said cushioning coupler is formed as a bellows.

7. A prosthetic intervertebral disc according to claim 5, wherein said pivoting ball has a neck portion having a diameter less than a diameter of the ball; and the spherical recess has a narrowing port engageable with the neck portion of the ball wherein a port diameter of the narrowing port is smaller than a diameter of the spherical recess for ensuring a stable coupling of the ball with the recess; the diameter of the ball being equal to that of the spherical recess.

8. A prosthetic intervertebral disc according to claim 5, wherein said cushioning coupler includes a cushioning sac filled with a viscous liquid therein, said coupler having an inflating valve protruding outwardly through the lower fusion member.

* * * * *